United States Patent [19]

Haji et al.

[11] Patent Number: 4,777,302

[45] Date of Patent: Oct. 11, 1988

[54] METHOD FOR HYDROGENATING AN ALDEHYDE AND/OR A KETONE

[75] Inventors: Junzo Haji; Ichiro Yokotake, both of Yokohama; Nobuyuki Murai; Toshihiro Kawakami, both of Yokkaichi, all of Japan

[73] Assignee: Mitsubishi Chemical Industries Limited, Tokyo, Japan

[21] Appl. No.: 79,407

[22] Filed: Jul. 30, 1987

[30] Foreign Application Priority Data

Aug. 20, 1986 [JP] Japan .................................. 61-195030

[51] Int. Cl.$^4$ ............................................. C07C 29/14
[52] U.S. Cl. ..................................... 568/862; 568/863
[58] Field of Search ............... 568/846, 861, 862, 863, 568/880

[56] References Cited

U.S. PATENT DOCUMENTS

| 2,868,847 | 1/1959 | Boyer | 568/863 |
| 3,260,759 | 7/1966 | Skinner | 568/862 |
| 4,317,946 | 3/1982 | Costa | 568/862 |
| 4,321,414 | 3/1982 | Costa | 568/862 |
| 4,503,274 | 3/1985 | Areba | 568/863 |
| 4,520,211 | 5/1985 | Lepper et al. | 568/863 |
| 4,694,113 | 9/1987 | Gauthier et al. | 568/863 |

Primary Examiner—Werren B. Lone
Attorney, Agent, or Firm—Oblon, Fisher, Spivak, McClelland & Maier

[57] ABSTRACT

A method for hydrogenating an aldehyde and/or a ketone in the presence of a ruthenium catalyst, wherein said ruthenium catalyst is obtained by reducing an alkali metal ruthenate with a reducing agent selected from the group consisting of methanol, formaldehyde and formic acid.

12 Claims, No Drawings

METHOD FOR HYDROGENATING AN ALDEHYDE AND/OR A KETONE

BACKGROUND OF THE INVENTION

1. Field of the Invention

The present invention relates to a method for hydrogenating an aldehyde and/or a ketone to obtain an alcohol useful as a raw material for various chemical industries or as a high performance solvent.

2. Discussion of Background

It has been known to use a ruthenium catalyst for hydrogenating an aldehyde or a ketone. (For example, see "Practical Catalysts for Respective Reactions" published by Kagaku Kogyo Sha, p.176–191.)

For the production of a ruthenium catalyst, it is common to employ a method wherein an aqueous solution of ruthenium chloride is impregnated within a carrier, then washed with water and dried, and finally reduced with hydrogen gas. (For example, see Platinum Metal Rev. 6, p.12–19 (1962).) However, the ruthenium catalyst obtained by this method is still poor in its catalytic activity, and a higher activity is desired particularly when an expensive metal such as ruthenium is used as a catalyst on an industrial scale.

SUMMARY OF THE INVENTION

It is an object of the present invention to overcome the above-mentioned problem relating to the ruthenium catalyst for hydrogenating an aldehyde or a ketone, and to provide a ruthenium catalyst having high activity, high selectivity and long useful life.

The present invention provides a method for hydrogenating an aldehyde and/or a ketone in the presence of a ruthenium catalyst, wherein said ruthenium catalyst is obtained by reducing an alkali metal ruthenate with a reducing agent selected from the group consisting of methanol, formaldehyde and formic acid.

DETAILED DESCRIPTION OF THE PREFERRED EMBODIMENTS

Now, the present invention will be described in detail.

The aldehyde and/or the ketone to be treated by the present invention, is an aliphatic aldehyde and/or ketone which may have substituents. Specifically, they include an aliphatic aldehyde which may have an acetoxy group or a hydroxy group as the substituent, such as acetaldehyde, propionaldehyde, n-butylaldehyde, isobutylaldehyde, 1-acetoxy-butane-4-al or 1-hydroxy-butane-4-al, and an aliphatic ketone which may have an acetoxy group or a hydroxyl group as the substituent, such as dimethyl ketone, methyl ethyl ketone, 1-acetoxy-butane-2-one or 1-hydroxy-butane-2-one.

The alkali metal ruthenate as the starting material for the production of the ruthenium catalyst, includes sodium ruthenate and potassium ruthenate. Particularly preferred is sodium ruthenate.

The reducing agent is usually employed in the form of an aqueous solution. The methanol, formaldehyde or formic acid may be used in an amount sufficient to reduce the alkali metal ruthenate to ruthenium metal. It may, of course, be used in an access amount. Usually, its amount is selected within a range of from 1 to 500 mols per mol of ruthenium metal.

The ruthenium catalyst of the present invention can be obtained by reducing the alkali metal ruthenate with a reducing agent selected from the group consisting of methanol, formaldehyde and formic acid. It is preferably supported on a carrier. There is no particular restriction as to the carrier to be used. It may be active carbon, alumina or silica. However, it is preferred to use active carbon as the carrier, particularly for the production of a highly active catalyst. For the preparation of a carrier-supported catalyst, an aqueous solution or an aqueous alkaline solution of an alkali metal ruthenate is first impregnated within a carrier.

The alkali metal ruthenate is supported on the carrier preferably in an amount of from 0.1 to 10% by weight, more preferably from 0.5 to 5% by weight, in terms of ruthenium metal based on the carrier. The alkali metal ruthenate supported on the carrier is reduced by a reducing agent substantially to metallic ruthenium for use as the catalyst.

The ruthenium catalyst thus supported on the carrier is then washed with water to remove the alkali metal component. The alkali metal concentration in the catalyst is controlled preferably to a level of not higher than 2,000 ppm, more preferably not higher than 500 ppm, whereby a high hydrogenation performance can be obtained.

Commonly known hydrogenation reaction conditions may suitably be employed as the conditions of the production of an alcohol by hydrogenating the aldehyde and/or the ketone by using the ruthenium catalyst. There is no particular restriction as to the reaction conditions. However, the hydrogen pressure is selected usually within a range of from about atmospheric pressure to 100 kg/cm², more preferably from 10 to 60 kg/cm², and the reaction temperature is selected preferably within a range of from 15° to 150° C., more preferably from 20° to 100° C.

The aldehyde and/or the ketone for the reaction may be used alone or in combination as a mixture of different types. It is, of cause, possible to employ an alcohol, an ester for an aliphatic hydrocarbon, as a solvent.

Now, the present invention will be described in further detail with reference to Examples. However, it should be understood that the present invention is by no means restricted to such specific Examples.

EXAMPLE 1

Water-containing columnar active carbon (dry weight: 10 g) having a diameter of 4 mm and previously washed with water was added at room temperature to 40 g of an aqueous alkaline solution of sodium ruthenate (containing 0.25% by weight of ruthenium metal), and the mixture was maintained at a temperature of 60° C. for one hour to have the ruthenium salt adsorbed on the active carbon.

After filtration, the ruthenium salt supported on active carbon was added at room temperature to 30 g of an aqueous solution containing 0.2 g of formaldehyde, and the mixture was maintained at a temperature of 60° C. for one hour for reducing treatment. After filtration, ruthenium supported on active carbon thus obtained was subjected to water washing treatment five times with 100 g of heated water of 60° C. Then, after filtration once more, the catalyst was dried at 120° C. for two hours under a nitrogen stream, and the water content was completely removed to obtain 10.1 g of the catalyst. The catalyst thus obtained had 1% by weight of ruthenium metal supported thereon.

Then, 1.5 g of the catalyst thus obtained and 50 g of a mixture comprising 2% by weight of 1-acetoxybutane-4-al (hereinafter referred to simply as ABD), 2% by weight of 1-hydroxy-butane-2-one (hereinafter referred to simply as HMEK), 1.5% by weight of 1-acetoxy-butane-2-one (hereinafter referred to simply as MEKA) and 1,4-diacetoxybutane as the solvent, were charged into a stainless steel shaking autoclave having an internal capacity of 100 cc, and the hydrogenation reaction was conducted under a hydrogen pressure of 30 kg/cm$^2$ at a reaction temperature of 60° C. for 4 hours. After the completion of the reaction, the reaction solution was separated from the catalyst and analyzed by gas chromatography. The results are shown in Table 1. ABD, HMEK and MEKA were selectively converted to the corresponding alcohols, respectively. The ABD, HMEK and MEKA conversions were calculated in accordance with the following formulas, respectively.

ABD conversion (wt %) =

$$\left(1 - \frac{\text{Unreacted } ABD \text{ weight}}{\text{Charged } ABD \text{ weight}}\right) \times 100$$

HMEK conversion (wt %) =

$$\left(1 - \frac{\text{Unreacted } HMEK \text{ weight}}{\text{Charged } HMEK \text{ weight}}\right) \times 100$$

MEKA conversion (wt %) =

$$\left(1 - \frac{\text{Unreacted } MEKA \text{ weight}}{\text{Charged } MEKA \text{ weight}}\right) \times 100$$

COMPARATIVE EXAMPLE 1

The operation was conducted in the same manner as in Example 1 except that the aqueous alkaline solution of sodium ruthernate was changed to an aqueous hydrochloric acid of ruthenuim chloride. The results are shown in Table 1.

COMPARATIVE EXAMPLE 2

Water-containing columnar active carbon (dry weight: 10 g) having a diameter of 4 mm and previously washed with water was added at room temperature to 40 g of an aqueous alkaline solution of sodium ruthenate (containing 0.25% by weight of ruthenium metal), and the mixture was maintained at a temperature of 60° C. for one hour to have the ruthenium salt adsorbed on the active carbon. After filtration, the ruthenium salt supported on active carbon was washed five times with 100 g of heated water of 60° C. After filtration once more, the catalyst was reduced under a hydrogen stream at a temperature of 200° C. for 3 hours, to obtain 10.1 g of a catalyst. By using 1.5 g of the catalyst thus obtained, the hydrogenation reaction was conducted in the same manner as in Example 1, and the analysis was conducted in the same manner as in Example 1. The results are shown in Table 1.

COMPARATIVE EXAMPLES 3 and 4

The operation was conducted in the same manner as in Comparative Example 2 except that the aqueous alkaline solution of sodium ruthenate was changed to an aqueous hydrochloric acid of ruthenium chloride or an aqueous nitric acid of ruthenium nitrate.

COMPARATIVE EXAMPLE 5

The operation was conducted in the same manner as in Example 1 except that the reducing agent was changed to hydrazine hydrochloride. The results are shown in Table 1.

EXAMPLE 2

The operation was conducted in the same manner as in Example 1 except that an aqueous alkaline solution of sodium ruthenate (containing 1% by weight of ruthenium metal) was used. The results are shown in Table 1.

In the catalyst of this Example, ruthenium metal was supported in an amount of 3% by weight, and the sodium content was 400 ppm

EXAMPLE 3

The operation was conducted in the same manner as in Example 2 except that the drying treatment was conducted under an air stream at a temperature of 120° C. for two hours. The results are shown in Table 1.

EXAMPLE 4

In the same manner as in Example 2 except that the amount of water for washing was changed, a catalyst having a sodium content of 2,500 ppm was obtained. By using this catalyst, the hydrogenation reaction was conducted in the same manner as in Example 1. The results are shown in Table 1.

EXAMPLE 5

The operation was conducted in the same manner as in Example 1 except that the reducing agent was changed to 0.1 g of methanol. The results are shown in Table 1.

EXAMPLE 6

The operation was conducted in the same manner as in Example 1 except that the reducing agent was changed to 0.2 g of formic acid. The results are shown in Table 1.

TABLE 1

| | Ruthenium salt | Reducing agent | Reducing temperature (°C.) | Drying atmosphere | Supported ruthenium (wt %) | Sodium content (ppm) | Concentration (wt %) | | |
|---|---|---|---|---|---|---|---|---|---|
| | | | | | | | ABD | HMEK | MEKA |
| Example | | | | | | | | | |
| 1 | Na$_2$RuO$_4$ | HCHO | 60 | N$_2$ | 1 | 350 | 98 | 38 | 15 |
| 2 | " | " | " | " | 3 | 400 | 100 | 96 | 89 |
| 3 | " | " | " | Air | 3 | 400 | 100 | 90 | 86 |
| 4 | " | " | " | N$_2$ | 3 | 2,500 | 83 | 15 | 5 |
| 5 | " | CH$_3$OH | " | " | " | 300 | 91 | 27 | 15 |
| 6 | " | HCOOH | " | " | " | 350 | 99 | 30 | 13 |
| Comparative Example | | | | | | | | | |
| 1 | RuCl$_3$ | " | " | N$_2$ | 1 | — | 8.1 | 0 | 0 |

TABLE 1-continued

| | Ruthenium salt | Reducing agent | Reducing temperature (°C.) | Drying atmosphere | Supported ruthenium (wt %) | Sodium content (ppm) | Concentration (wt %) | | |
|---|---|---|---|---|---|---|---|---|---|
| | | | | | | | ABD | HMEK | MEKA |
| 2 | Na$_2$RuO$_4$ | H$_2$ | 200 | " | 1 | 350 | 34 | 11 | 0 |
| 3 | RuCl$_3$ | " | " | " | 1 | — | 60 | 11 | 1 |
| 4 | Ru(NO$_3$)$_3$ | " | " | " | 1 | — | 37 | 20 | 0 |
| 5 | Na$_2$RuO$_4$ | N$_2$H$_4$.HCl | 60 | " | 1 | 350 | 67 | 8 | 0.5 |

EXAMPLE 7

12 g of the same catalyst as used in Example 2 was packed into a stainless steel reaction tube having an effective cross-sectional area of 2 cm$^2$, of a continuous flow reaction apparatus, and the same hydrogenation raw material solution as used in Example 1 was continuously charged at a rate of 50 g per hour under a hydrogen pressure of 40 kg/cm$^2$ and at a reaction temperature of 80° C. The reaction was conducted for 1,000 hours to determine the useful life of the catalyst. The results are shown in Table 2.

TABLE 2

| | Reaction time (hrs) | Concentration (wt %) | | |
|---|---|---|---|---|
| | | ABD | HMEK | MEKA |
| Example 7 | 20 | 100 | 96 | 80 |
| | 300 | 100 | 89 | 60 |
| | 600 | 100 | 83 | 48 |
| | 1000 | 100 | 70 | 38 |

The ruthenium catalyst used in the present invention, which is obtained by reducing an alkali metal ruthenate with a certain reducing agent selected from the group consisting of methanol, formaldehyde and formic acid, has high activity, high selectivity and long useful life, whereby it is possible to obtain from a aldehyde and/or a ketone the corresponding alcohol in high selectivity.

What is claimed is:

1. A method for hydrogenating an aliphatic aldehyde, an aliphatic ketone or mixtures thereof to produce the corresponding alcohol or alcohols, comprising:
hydrogenating said aldehyde, ketone or mixture thereof in the presence of a ruthenium catalyst prepared by reducing an alkali metal ruthenate with a reducing agent selected from the group consisting of methanol, formaldehyde and formic acid.

2. The method of claim 1, wherein the alkali metal concentration in said ruthenium catalyst is not greater than 2000 ppm.

3. The method of claim 1, wherein the amount of said reducing agent employed ranges from 1 to 500 moles per mole of ruthenium metal.

4. The method of claim 1, wherein said ruthenium catalyst is prepared by adsorbing alkali metal ruthenate from an aqueous solution containing the same on a carrier, and then reducing the absorbed ruthenate with said reducing agent.

5. The method of claim 1, wherein the alkali metal ruthenate is supported on a carrier in an amount ranging from 0.1 to 10% by weight, calculated as ruthenium metal, relative to the carrier.

6. The method of claim 1, wherein said carrier is active carbon.

7. The method of claim 1, wherein said aliphatic aldehyde is a member selected from the group consisting of acetaldehyde, propionaldehyde, n-butylaldehyde, isobutylaldehyde, 1-acetoxybutane-4-al and 1-hydroxybutane-4-al.

8. The method of claim 1, wherein said aliphatic ketone is a member selected from the group consisting of dimethylketone, methylethylketone, 1-acetoxybutane-2-one and 1-khyroxybutane-2-one.

9. The method of claim 1, wherein said alkali metal ruthenate is sodium ruthenate or potassium ruthenate.

10. The method of claim 1, wherein the hydrogenation of said aldehyde or ketone reactant occurs at a hydrogen pressure ranging from about atmospheric pressure to 100 kg/cm$^2$ over a temperature ranging from 15° and 150° C.

11. The method of claim 10, wherein said hydrogen pressure ranges from 10 to 60 kg/cm$^2$ and said reaction temperature ranges from 20° and 100° C.

12. The method of claim 1, wherein the hydrogenation reaction is conducted in an alcohol, ester or aliphatic hydrocarbon solvent.

* * * * *